United States Patent [19]

Bellamy

[11] 4,094,742

[45] June 13, 1978

[54] PRODUCTION OF ETHANOL FROM CELLULOSE USING A THERMOPHILIC MIXED CULTURE

[75] Inventor: Winthrop D. Bellamy, Schenectady, N.Y.

[73] Assignee: General Electric Company, Schenectady, N.Y.

[21] Appl. No.: 774,380

[22] Filed: Mar. 4, 1977

[51] Int. Cl.$^2$ .............................................. C12C 11/38
[52] U.S. Cl. ....................................... 195/33; 195/65; 195/111
[58] Field of Search ...................... 195/13, 33, 96, 81, 195/111, 66 R, 65, 62

[56] References Cited

U.S. PATENT DOCUMENTS

| | | | |
|---|---|---|---|
| 3,711,392 | 1/1973 | Metzger | 195/111 X |
| 3,844,890 | 10/1974 | Horikoshi et al. | 195/62 |
| 3,983,002 | 9/1976 | Ohya et al. | 195/66 R |
| 3,990,944 | 11/1976 | Gauss et al. | 195/33 |
| 4,009,075 | 2/1977 | Hoge | 195/33 |

OTHER PUBLICATIONS

Atkinson et al., "Production of Alcohol by Bacillus Stereothermophilus", Chemical Abstracts, vol. 84, No. 1, p. 297 (1976), Abs. No. 3254f.

Clermont-Beaugiraud et al.,"Polysaccharidases from sporocytophaga myxococcoides: β-mannanase, cellulase, and xylanase", Chemical Abstracts, vol. 75, No. 5, p. 47 (1971), Abs. No. 30388y.

*Primary Examiner*—Raymond N. Jones
*Assistant Examiner*—Thomas G. Wiseman
*Attorney, Agent, or Firm*—Jane Binkowski; Joseph T. Cohen; Marvin Snyder

[57] ABSTRACT

A mixed culture of thermophilic cellulolytic sporocytophaga and thermophilic ethanol-producing bacillus is admixed with a suspension of cellulose in nutrient mineral broth and the resulting mixture is fermented at a pH ranging from 7 to 8 and at a temperature of 50° C to 65° C to produce ethanol.

10 Claims, No Drawings

PRODUCTION OF ETHANOL FROM CELLULOSE USING A THERMOPHILIC MIXED CULTURE

The present invention relates to a process for producing ethanol from cellulose through the combined growth of thermophilic cellulolytic sporocytophaga and an ethanol-producing thermophilic bacillus.

Cellulose is a solid natural polymer of glucose. In its native state or form, cellulose has a physical structure comprised of a mixture of crystalline and amorphous areas or regions. Chemical reagents react with or penetrate the amorphous regions much more readily than the crystalline regions. In a pure or relatively pure form, cellulose can be converted by a variety of techniques to useful products such as paper, sugar, ethanol and methane. Yeast fermentation of cellulose to produce ethanol must be preceded by a hydrolysis step because yeast cannot hydrolyze cellulose.

Thus far, only mesophilic cellulolytic sporocytophaga have been known in the art. The mesophilic cellulolytic sporocytophaga grow at temperatures of 20°-30° C and digest cellulose at a rate too slow to be useful. The present invention utilizes a novel thermophilic cellulolytic sporocytophaga which grows at elevated temperatures and which produces enzymes that digest cellulose at a rate substantially higher than those of its mesophilic counterparts, frequently by a factor of 2 to 4. Specifically, in the present invention, a novel mixed culture of a thermophilic cellulolytic sporocytophaga and a thermophilic ethanol-producing bacillus is used to produce ethanol from cellulose in a single fermentation step. The enzymes of the thermophilic cellulolytic sporocytophaga hydrolyze cellulose to soluble sugars and the enzymes of the thermophilic bacillus convert the soluble sugars to ethanol. By the term soluble sugars herein it is meant sugars soluble in water at a temperature of 50° C. One of the advantages of the present invention is that it obviates the necessity for more complex conventional approaches which require application of external chemicals at high cost with the concomitant residue disposal problem associated with the added chemicals.

Briefly stated, the present process comprises admixing cellulose or a cellulosic material with nutrient mineral broth to form a suspension having a pH ranging from about 7 to 8, admixing with said suspension a mixed culture of thermophilic cellulolytic sporocytophaga and thermophilic ethanol-producing bacillus, and fermenting the resulting mixture at a pH ranging from about 7 to 8 and at a temperature ranging from about 50° C to about 65° C to produce at least a significant amount of ethanol. By a cellulosic material it is meant herein cellulose itself or a material which has been treated to make the cellulose component available, in at least a major amount, or preferably at least a substantial amount, for contact with the mixed culture. Also, by a significant amount of ethanol it is meant herein ethanol in an amount of at least about 10% by weight of the cellulose present in the fermentor.

In carrying out the present process the source of cellulose is not critical and native or natural cellulosic material as well as waste cellulose are useful.

Cellulose is the major constituent of vegetable tissues. The bulk of renewable organic matter on earth consists of lignocellulose. Except in the form of cotton and some bacterial polymers, cellulose does not occur pure naturally but is present in the tissue of land plants complexed with lower molecular weight, alkali-soluble polysaccharides collectively termed hemicelluloses and with lignin, a high molecular weight three-dimensional random polymer of phenylpropane alcohols. Lignin in the form of a protective covering prevents enzymatic hydrolysis of the cellulose to soluble sugars. The greater the lignin content of lignocellulosic material, the more resistant is its cellulose component to enzyme attack. Representative of the lignocellulosic materials are wood, manure fiber, and straw. Wood contains about 50% cellulose whereas cotton fibers contain about 98% cellulose.

Representative of the waste cellulosic material which are useful herein as a source of cellulose are industrial cellulosic wastes such as boxes, newsprint and paper bags and agricultural wastes such as bagasse.

In the present invention, the source of cellulose, i.e. natural or waste, need only be treated, if necessary, to make its cellulose component available at least in a major amount, preferably higher than 60% by weight of the cellulose present, for contact with the mixed culture. Such treatment may be physical or chemical.

According to one method the lignocellulosic material is comminuted to a fine particle size, preferably less than 100 microns, to expose and make available at least a major portion of the cellulose component for contact with the present mixed culture during fermentation. Comminutation can be carried out by conventional techniques such as by mechanical grinding or pulverizing the lignocellulosic material.

Alternatively, to free the cellulose component, the lignocellulosic material can be treated with acid or alkali metal hydroxide which penetrate the lignin and degrade or depolymerize it sufficiently to make the cellulose available for contact with the present mixed culture. For example, the lignocellulosic material in its natural form, i.e., hull, stalk or blade, or preferably in particulate form, is immersed in an aqueous metal hydroxide which may range in concentration from about 5% to 50% by weight of the alkali metal hydroxide, preferably sodium hydroxide, and preferably at an elevated temperature which may range up to 100° C. The alkali-treated material can then be recovered by conventional techniques, such as decantation or filtration, and then treated with acid, such as hydrochloric acid, to bring it to the desired pH range of 7 to 8. The particular concentration of alkali metal hydroxide, its temperature and the period of time of immersion of the lignocellulosic material therein are determinable empirically and depend largely on the amount of lignin present and the degree of degradation or disruption of lignin desired.

The present fermentation must be carried out under submerged condition. The present fermentation medium has a pH ranging from about 7 to 8 and it is comprised of a suspension of solid particulate or fibrous cellulosic material in aqueous nutrient mineral broth. The suspension can be formed in a standard manner by simply admixing the particulate or fibrous cellulosic material with the nutrient broth in proper amounts. The amount of cellulosic material in the suspension should be sufficient to provide at least significant contact with the mixed culture to allow fermentation to proceed at least at a practical rate. To be useful, the amount of solid cellulosic material present in the suspension should be at least about 2% by weight of the total suspension, and preferably, it ranges from about 5% by weight to about 50% by weight of the suspension. Amounts of cellulosic material higher than about 50% by weight of the suspension absorb a substantial amount of water making it too difficult to form a suspension.

The fermentation medium must have a pH ranging from about 7 to 8 and should be maintained at such pH during fermentation. At a pH below 7, the thermophilic cellulolytic sporocytophaga does not grow whereas at a pH above 8 it grows very slowly. Preferably, for optimum growth rate of the present mixed culture, the pH of the fermentation medium should range from 7.2 to 7.8. The pH of the contents of the fermentor during fermentation can be monitored continuously by conventional means such as a pH probe. Whenever necessary during fermentation, the contents of the fermentor can be adjusted to the proper pH in a conventional manner by the addition of suitable acid or alkali such as hydrochloric acid or sodium hydroxide.

The solid cellulosic material used in forming the fermentation medium is comminuted, if necessary, by standard techniques such as grinding or pulverizing to fine particulate or fibrous form. The particulate cellulosic material should have a size less than about 1,000 microns and preferably less than about 100 microns. The fibrous cellulosic material should have a diameter less than about 1,000 microns and preferably finer. The finer the cellulosic material, the more surface area is available for contact with the mixed culture and thereby the more effective is the digestion of the cellulose, i.e., the faster is the rate of fermentation of the cellulose to produce ethanol. Also, as a practical matter, the cellulosic material should contain cellulose in an amount of at least 30% by weight, and preferably at least 50% by weight or higher of the total amount of cellulosic material used in forming the suspension. Also, preferably, the cellulosic material has a pH ranging from about 7 to 8.

The particular nutrient mineral broth used is not critical, and preferably, it has a pH of about 7 to 8 which is necessary for growing the mixed culture organisms. The term broth herein includes a solution as well as a suspension. Specifically, the broth is largely inorganic and includes a number of minerals in solution to provide the major nutrient ions such as sodium, potassium, phosphate, sulfate, magnesium and iron and usually includes an organic chelating agent to keep iron from precipitating. The absolute concentrations of the nutrients in the broth are not critical as long as they are present in adequate amounts for the mixed culture organisms to grow but not so high as to inhibit growth. Standard bacteriological growing media are useful herein as nutrient mineral broth because they all contain the major ions necessary for bacteria growth, and the exact formulation may be modified in the standard manner depending on the composition of the particular cellulosic material, i.e., the extent to which the nutrients are already contained in the substrate.

The mixed culture of the present invention is comprised of a thermophilic cellulolytic gram-negative sporocytophaga and an ethanol-producing gram-positive thermophilic bacillus.

The ethanol-producing gram-positive thermophilic bacillus of the present invention is a strain which grows at temperatures within the range of from about 50° C to 65° C and at a pH ranging from 7 to 8 and produces ethanol at at least a practical rate, i.e., at least about 0.25 gram per liter × hour. The Eighth Edition of Bergey's Manual of Determinative Bacteriology, The Williams & Wilkins Co., 1974, discloses at page 540 that *Bacillus stereothermophilus* grows at temperatures from a minimum range of 30° C to 45° C to a maximum range of 65° C to 75° C, and that *Bacillus coagulans* grows at temperatures from a minimum range of 15° C to 25° C to a maximum range of 55° C to 60° C. Therefore, representative species which can be utilized in accordance with the present invention include *Bacillus stereothermophilus* and *Bacillus coagulans*. Cultures of these bacilli are contained in the American Type Culture Collection located in Washington, D.C. and in other repositories. It is believed that the present thermophilic cellulolytic gram-positive bacillus is a *Bacillus stereothermophilus* which grows slowly at 65° C.

The present mixed culture can be formed in a conventional manner, i.e., the thermophilic cellulolytic sporocytophaga and ethanol-producing bacillus can be grown together submerged in a standard nutrient solution at temperatures ranging from about 50° C to about 65° C.

The present mixed culture comprised of thermophilic cellulolytic gram-negative sporocytophaga designated "US" and ethanol-producing gram-positive thermophilic bacillus designated "OK" was deposited with the U.S. Dpartment of Agriculture. This mixed culture (NRRL B-11077) is identified as follows:

This sporocytophaga culture US was isolated from a sample of soil and decaying wood collected at the base of an old elm stump in the Schenectady, NY, area during a search for thermophilic cellulolytic microorganisms. After enrichment growth in an aqueous medium which was comprised of, on the basis of 100 ml of water, 0.05 gram yeast extract, 0.05 gram tryptone, particulate filter paper and soil samples, it was subcultured on an aqueous medium which was comprised of, on the basis of 100 ml of water, 0.1 gram yeast extract, 1 gram tryptone, M/15 phosphate buffer pH 7.0 and particulate filter paper. This sporocytophaga strain was found to produce a bright yellow to orange pigment when grown on cellulose. It did not initiate growth in the presence of air but grew up to the surface after submerged growth had become established. This sporocytophaga strain grows as a long thin gram-negative rod with a diameter of about 0.7 micron and a variable length up to several microns with an enlarged terminal spore. All attempts to grow this sporocytophaga in a pure culture have failed; it is always associated with a gram-positive thermophilic bacillus. This strain US of sporocytophaga will survive 90° C for 10 minutes but not 20 minutes, and 96° C for 4 minutes but not 7 minutes. In a media freshly inoculated with the present mixed culture, the bacillus rapidly established an aerobic and anaerobic growth, the sporocytophaga grew more slowly and initiated cellulose digestion and pigment production under anaerobic conditions. No yellow pigment was produced by the sporocytophaga when grown in a medium containing glucose as the carbohydrate source. The optimum pH for this sporocytophaga was found to be 7.5 to 7.8; it did not initiate growth at 6.5, nor above 8.5. The optimum temperature for its growth was found to be 55° C to 65° C. Specifically, growth of the sporocytophaga was abundant at 45° C but very slow or absent at 40° C and 70° C.

This strain OK of ethanol-producing gram-positive thermophilic bacillus was isolated from decaying vegetation and soil obtained from an anomolous hot earth area in Yellowstone National Park. It was found to grow on a rich medium such as Luria broth. It did not grow in unsupplemented mineral broth but did grow in mineral broth supplemented with 0.2% yeast extract. It grew from 40° C to 60° C. It did not grow at 70° C nor at 30° C. It is a large gram-positive rod with a diameter of about 1 micron and a length ranging from 2.5 to about 5 microns with a single spore. It fermented both glucose and cellobiose. It exhibited proteolytic action when grown on litmus milk.

A subculture of this mixed culture can be obtained from the permanent collection of the Northern Marketing and Nutrient Research Division, Agricultural Service, U.S. Department of Agriculture, Peoria, Illinois, U.S.A.

The present fermentation is carried out at a temperature ranging from about 50° C to 65° C. The particular fermentation temperature used depends largely on the growth rate at such temperature of the particular ethanol-producing bacillus used. Fermentation temperatures below 50° C are not useful because the sporocytophaga grows too slowly whereas at temperatures above 65° C the bacilli grow not at all or too slowly to be useful. Fermentation temperatures ranging from about 55° C to 60° C usually result in optimum growth of the mixed culture of the present invention.

The present fermentation is carried out in a closed vessel or fermentor. The mixed culture, usually suspended in nutrient mineral broth, is preferably admixed with the fermentation medium so that it is distributed throughout the suspension at least significantly uniformly. The present fermentation is anaerobic but it does not require the bubbling of carbon dioxide gas through the fermentating medium or mass because the present mixed culture of organisms gives off carbon dioxide gas during fermentation. Also, the evolution of such carbon dioxide gas maintains the fermenting mass in sufficient suspension so as to eliminate the need for external agitating means.

The present fermentation may be carried out as a batch process. It may also be a continuous process by adding additional cellulosic material to the fermentor to replenish cellulose which has been digested and removed. The atmosphere in the fermentor during fermentation may be at atmospheric pressure or it may be a partial vacuum. At atmospheric pressure, as ethanol accumulates in the fermentor, it slows fermentation and eventually stops it substantially. In a batch process carried out at atmospheric pressure, the residence time in the fermentor may vary and it is determinable empirically by determining when production of ethanol ceases. This can be done by a number of techniques such as, for example, removing samples of the fermenting mass over a period of time and determining their ethanol content in a standard manner. When fermentation carried out at atmospheric pressure is completed, the contents of the fermentor are then treated to separate and recover its ethanol component. This can be carried out by subjecting the contents of the fermentor to a temperature ranging from about 78° C to about 85° C to distill off the ethanol or alternatively, subjecting the fermentor contents to temperatures below 78° C, preferably from about 50° C to 70° C, and a partial vacuum.

A partial vacuum in the fermentor is preferred since it results in yields of ethanol substantially higher than those produced at atmospheric pressure. For example, at atmospheric pressure the yield of ethanol based on cellulose may range from about 10% to about 20% of theoretical whereas with a partial vacuum the yield of ethanol can range from 40% to 80% or higher of theoretical. The partial vacuum distills off ethanol as fast as it is formed and the amount of ethanol produced, is limited largely by the amount of cellulose present in the fermentor. The partial vacuum need only be sufficient at the particular fermenting temperature to vaporize the ethanol produced during fermentation and also sufficient to withdraw the ethanol vapor from the fermentor. Usually, such partial vacuum ranges in pressure from about 100 mm Hg. to about 400 mm Hg.

When a partial vacuum is used during fermentation, it is preferred to flow a gas through the atmosphere in the fermentor to help sweep the ethanol vapor out of the fermentor. The gas may be one to which the contents of the fermentor are inert such as nitrogen, or it may be a basic gas such as ammonia or an acidic gas such as $CO_2$ to help maintain the proper pH during fermentation. The flow of gas can vary and is determinable empirically. The carbon dioxide gas also improves the growth of the sporocytophaga by replenishing carbonate or $CO_2$ gas removed by the partial vacuum, because $CO_2$ is required for its effective growth.

The invention is further illustrated by the following example.

EXAMPLE 1

In this example the mixed culture assigned the number NRRL B-11077 and comprised of thermophilic cellulolytic sporocytophaga "US" and thermophilic cellulolytic ethanol-producing bacillus "OK" was used. The nutrient mineral broth used contained $(NH_4)_2SO_4$, 5.0 grams; NaCl, 1 gram; $MgSO_4 \cdot 7H_2O$, 0.2 gram; $ZnSO_4 \cdot 7H_2O$, 0.008 gram; $FeSO_4 \cdot 7H_2O$, 0.2 gram; $MnSO_4 \cdot 4H_2O$, 0.02 gram; CaCl, 0.02 gram; Versenol, 0.2 gram; and M/15 phosphate buffer per liter of distilled water and was adjusted to pH 7.5.

The apparatus used was comprised of a one liter fermentation vessel associated with a 500 ml water trap, and a 50 ml alcohol trap, plus necessary connectors, and condensers. The fermentor vessel had a pH probe and an inlet for either carbon dioxide gas or ammonia. The water trap had a vacuum gauge, and the condenser in the alcohol trap operated on ground water at 15° C to 18° C. Both the fermentor and the water trap were maintained at desired temperature by thermostated glascol heaters. During operation, the pH and the partial vacuum in the fermentor vessel were maintained at desired values by manual operations. The pH of the fermenting mixture was maintained at 7.5 by periodic addition of ammonia as ammonium hydroxide because organic acids were produced during growth. Carbon dioxide gas from an associated lecture cylinder was periodically bled into the atmosphere of the fermentor slowly to help sweep out the ethanol vapor from the fermentor atmosphere and to replace the carbon dioxide removed by the partial vacuum.

A suspension of 500 ml of the mineral broth plus 0.5 gram yeast extract and 5 grams of Whatman #1 filter paper which had a particle size ranging from about 100 to 1,000 microns was inoculated with the present mixed culture (NRRL B-11077) at room temperature. The filter paper consists of cellulose only. Although yeast extract was included in the mineral broth, it is not a required nutrient for growth of this mixed culture, and specifically, it is not required for growth of the ethanol-producing bacillus in the present mixed culture since the sporocytophaga provides the required nutrients supplied by the yeast extract.

The resulting fermentation mass was maintained in the closed fermentation vessel at 55° C at a pH ranging from 7 to 8 at atmospheric pressure for 12 hours. At the end of that time, there was heavy growth of the mixed culture in the fermentation vessel. The atmospheric pressure was then gradually lowered to 153 mm Hg. The fermentation vessel was maintained at 55° C, the water trap at 40° C, and the ethanol trap was at room temperature which was about 25° C while the condenser water was 15° C to 18° C. Under these conditions, 10 ml of 50% ethanol was collected in the trap during the first two hours, and approximately 2 ml of 50% ethanol per hour was collected for the next 7 hours. It was necessary to return the water from the water trap to the fermentation vessel to make up the water lost at the end of the two hours and five hours. The yield of ethanol based on the amount of cellulose was about 40% of theoretical.

What is claimed is:

1. A process for fermenting cellulose to produce ethanol by the combined growth of a mixed culture of thermophilic cellulolytic gram-negative sporocytophaga and thermophilic ethanol-producing gram-positive bacillus said thermophilic cellulolytic gram-negative sporocytophaga always being associated with a gram-positive thermophilic bacillus, which comprises providing a particulate or fibrous cellulosic material wherein at least a major amount of the cellulose component is exposed, admixing an aqueous nutrient mineral broth with said particulate cellulosic material to form a suspension having a pH ranging from about 7 to 8, said aqueous nutrient mineral broth being a source of nutrients for said mixed culture, admixing said mixed culture with said suspension, and fermenting the resulting mixture at a temperature ranging from about 50° C to about 65° C and at a pH of about 7 to 8 to produce at least a significant amount of ethanol and recovering said ethanol.

2. A process according to claim 1 wherein said cellulosic material is cellulose.

3. A process according to claim 1 wherein said pH ranges from 7.2 to 7.8.

4. A process according to claim 1 wherein said fermentation temperature ranges from 55° C to 65° C.

5. A process for fermenting cellulose to produce ethanol by the combined growth of a mixed culture of thermophilic cellulolytic gram-negative sporocytophaga and thermophilic ethanol-producing gram-positive bacillus, said thermophilic cellulolytic gram-negative sporocytophaga always being associated with a gram-positive thermophilic bacillus, which comprises providing a particulate or fibrous cellulosic material wherein at least a major amount of the cellulose component is exposed, admixing an aqueous nutrient mineral broth with said cellulosic material forming a suspension having a pH ranging from 7 to 8, said aqueous nutrient mineral broth being a source of nutrients for said mixed culture, admixing said mixed culture with said suspension, and fermenting the resulting mixture at a temperature ranging from about 50° C to about 65° C and at a pH of about 7 to 8 in an atmosphere which is a partial vacuum to produce at least a significant amount of ethanol, said partial vacuum being sufficient to vaporize said ethanol at said fermenting temperature, said partial vacuum vaporizing said ethanol and withdrawing said ethanol vapor from said fermentation and condensing said withdrawn ethanol vapor.

6. A process according to claim 5 wherein said partial vacuum ranges in pressure from about 100 mm Hg to about 400 mm Hg.

7. A process according to claim 5 wherein gas is flowed through said atmosphere.

8. A process according to claim 5 wherein said pH ranges from 7.2 to 7.8.

9. A process according to claim 5 wherein said cellulosic material is cellulose.

10. A process according to claim 5 wherein said fermenting temperature ranges from 55° C to 65° C.

* * * * *